United States Patent [19]
Janoff et al.

[11] Patent Number: 5,059,591
[45] Date of Patent: Oct. 22, 1991

[54] DRUG PREPARATIONS OF REDUCED TOXICITY

[75] Inventors: Andrew S. Janoff, Yardley, Pa.; Mircea C. Popescu, Plainsboro, N.J.; Carl R. Alving, Bethesda, Md.; Michael W. Fountain, Farragut, Tenn.; Robert P. Lenk, The Woodlands, Tex.; Marc J. Ostro, Princeton, N.J.; Paul A. Tremblay, Hamilton, N.J.; Alan L. Weiner, Lawrenceville, N.J.

[73] Assignee: The Liposome Company, Inc., Princeton, N.J.

[21] Appl. No.: 405,623

[22] Filed: Sep. 12, 1989

Related U.S. Application Data

[63] Continuation of Ser. No. 844,248, Mar. 24, 1986, Pat. No. 4,897,384, which is a continuation of Ser. No. 604,503, May 2, 1984, abandoned, which is a continuation-in-part of Ser. No. 498,268, May 26, 1983, abandoned.

[51] Int. Cl.⁵ .................. A61K 31/70; A61K 31/685; A61K 31/015; A61K 35/00
[52] U.S. Cl. ....................................... 514/31; 514/78; 514/766; 424/116; 424/450
[58] Field of Search .............. 514/78, 76, 34, 29, 514/27, 31, 786; 424/450, 116

[56] References Cited

U.S. PATENT DOCUMENTS

| | | | |
|---|---|---|---|
| 3,993,754 | 11/1976 | Rahman et al. | 514/12 |
| 4,075,324 | 2/1978 | Thizy et al. | 424/601 |
| 4,119,724 | 10/1978 | Thizy et al. | 424/45 |
| 4,160,827 | 7/1979 | Cho et al. | 514/78 |
| 4,256,632 | 3/1981 | Levin et al. | 530/322 |
| 4,263,428 | 4/1981 | Apple et al. | 536/17 A |
| 4,271,196 | 6/1981 | Schmidt | 514/772 |
| 4,272,525 | 6/1981 | Wright | 514/2 |
| 4,287,187 | 9/1981 | Hoeschele | 514/78 |
| 4,291,023 | 9/1981 | Hoeschele et al. | 514/23 |
| 4,291,027 | 9/1981 | Hoeschel et al. | 514/78 |
| 4,309,420 | 1/1982 | Ghyczy et al. | 514/78 |
| 4,332,795 | 6/1982 | Ghyczy et al. | 514/78 |
| 4,340,599 | 7/1982 | Lieb et al. | 514/120 |
| 4,346,084 | 8/1982 | Growdon et al. | 514/78 |
| 4,358,442 | 11/1982 | Wirtz-Peitz | 514/78 |
| 4,372,949 | 2/1983 | Kodama et al. | 514/78 |
| 4,396,630 | 8/1983 | Riedl et al. | 514/784 |
| 4,397,846 | 8/1983 | Weiner et al. | 514/78 |
| 4,411,894 | 10/1983 | Schrank et al. | 514/78 |
| 4,419,348 | 12/1983 | Rahman et al. | 514/23 |
| 4,430,330 | 2/1984 | Growdon et al. | 514/78 |

OTHER PUBLICATIONS

Schacht et al., 1983, "Aminoglycoside-Cell Receptor Interactions: Implications for Toxicity and In Vitro Models," Thirteenth International Congress of Chemotherapy.
Hokin, "Phospholipid Metabolism and Functional Activity of Nerve Cells", Structure and Function of Nervous Tissue, 1969, Bourne, ed., Academic Press, New York, vol. 3, pp.161–184.
Schact and Agranoff, "Phospholipid Labelling by [$^{32}$P]-Orthophosphate and [$^{3}$H]-Myo-Inositol in the Stimulated Goldfish Brain", J. Neurochem. 1972, vol. 19, pp. 1417–1421.
Margolis and Heller, "The Effect of Cholinergic and Other Pharmacological Agents on Brain Monophosphoinositide Turnover in Vivo", 1966, J. Pharmacol. Expt. Ther. 151:307–312.
Orsulakova et al., "Effect of Neomycin on Phosphoinositide Labelling and Calcium Binding in Guinea-Pig Inner Ear Tissues In Vivo and In Vitro", J. Neurochem., 1976, vol. 26, pp. 285–290.
Schibeci and Schacht, "Action of Neomycin on the Metabolism of Polyphosphoinositides in the Guinea Pig Kidney", Biochem. Pharmacol., 1977, 26:1769–1774.
Alexander et al., "Interaction of Aminoglycoside Antibiotics with Phospholipid Liposomes Studied by Microelectrophoresis", 1979, J. Antibiotics, 32:504–510.
Lodhi et al., "Ototoxicity of Aminoglycosides Correlated with Their Action on Monomolecular Films of Polyphosphoinositides", 1980, Biochem. Pharmacol, 29:597–601.
"The Pharmacological Basis of Therapeutics", 6th Edition, 1980, pp. 1233–1236, Goodman and Gilman, eds.
Medoff et al., "Antifungal Agents Useful in Therapy of Systemic Fungal Infections", 1983, Ann. Rev. Pharmacol. Toxicol. 23:303–330.
Bittman et al. (Readio & Bittman), "Equilibrium Binding of Amphotericin B and Its Methyl Ester and Borate Complex to Sterols", 1982, Biochim. Biophys. Acta, 685:219–224.
Taylor et al., "Amphotericin B in Liposomes: A Novel Therapy for Histoplasmosis", 1982, Ann. Rev. Respir. Dis. 125:610–611.
New et al., "Antileishmanial Activity of Amphotricin and Other Antifungal Antifungal Agents Entrapped in Liposomes", 1981, J. Antimicrob. Chemother. 8:371–381.
Goormaghtigh, et al., "Evidence of a Complex Between Adriamycin Derivatives and Cardiolipin: Possible Role in Cardiotoxicity", 1980, Biochm. Pharmacol. 29:3003–3010.
Goormaghtigh, et al., "Evidence of a Specific Complex Between Adriamycin and Negatively-Charged Phospholipids", 1980, Biochim. Biophys. Acta, 597:1–14.

(List continued on next page.)

*Primary Examiner*—John W. Rollins
*Attorney, Agent, or Firm*—Allen Bloom; Catherine L. Kurtz

[57] ABSTRACT

Preparations of drugs in admixture with certain ligands are described which, when administered to animals or humans, are less toxic than conventional drug preparations. Although the toxicity of the drug-ligand preparations described is greatly reduced, the drug retains pharmacological activity.

44 Claims, No Drawings

OTHER PUBLICATIONS

Goormaghtigh, et al., "Adriamycin Inactivates Cytochrome C Oxidase by Exclusion of the Enzyme from Its Cardiolipin Essential Environment", Biochim. Biophys. Res. Comm., 1982, vol. 104(1), pp. 314-320.

Forssen and Tokes, "Improved Therpaeutic Benefits of Doxorubicin by Entrapment in Anionic Liposomes", 1983, Cancer Res., 43:546-550.

Louie and Bau, "Structure of [Pt(en)5'-CMP)]$_2$2H$_2$O. An Example of Direct Platinum-Phosphate Bonding", 1977, J. Amer. Chem. Soc. 99:3874-76.

Goodgame et al., "Possible Mode of Action of Anti-Tumour Platinum Drugs: X-Ray Evidence for Cis Binding by Platinum of Two Inosine 5'-Monophosphate Molecules via the N(7) Positions", 1975, Biochim. Biophys. Acta., 378:153-157.

Bau et al., "Crystallographic Studies on Platinum-Nucleoside and Platinum-Nucleotide Complexes", 1977, J. Clin. Hematol. Oncol., Wadley Medical Bulletin, 7:51-61.

Davis and Abbitt, "Clinical Pharmacology of Antibacterial Drugs in the Uterus of the Mare", 1977, JAVMA 170(2):204-207.

Volanakis and Kaplan, "Specificity of C-Reactive Protein for Choline Phosphate Residues of Pneumococcal C-Polysaccharide (35323)", 1970, Proc. Soc. Exp. Biol. Med. 136:612-614.

Schacht, J., "Purification of Polyphosphoinositides by Chromatography on Immobilized Neomycin", 1978, J. Lipid Res. 19:1063-1067.

Nesmeyanova, et al., Chem. Abs. vol. 97:68366g, 1982.

Connors et al., Platinum Coordination Complexes in Cancer Chemotherapy, 1974.

DRUG PREPARATIONS OF REDUCED TOXICITY

This application is a continuation application of copending U.S. patent application Ser. No. 844,248 filed Mar. 24, 1986 now U.S. Pat. No. 4,897,384, which is in turn a continuation of U.S. patent application Ser. No. 604,503, filed May 2, 1984 now abandoned, which is in turn a continuation-in-part of U.S. patent application Ser. No. 498,268 filed May 26, 1983, now abandoned.

TABLE OF CONTENTS

1. Field of the Invention
2. Background of the Invention
   2.1. The Aminoglycoside Antibiotics
   2.2. The Polyene and Polyene Macrolide Antibiotics
   2.3. Adriamycin
   2.4. Cisplatin
   2.5. Concurrent Therapy
3. Summary of the Invention
4. Description of the Invention
   4.1. Aminoglycoside-Ligand Preparations
      4.1.1. Evidence of Complex Formation
   4.2. Polyene and Polyene Macrolide Antibiotic-Ligand Preparations
      4.2.1. Evidence of Complex Formation
   4.3. Adriamycin-Ligand Preparations
   4.4. Cisplatin-Ligand Preparations
5. Example: Streptomycin Preparations
   5.1. Reduced Toxicity of Streptomycin-Ligand Preparations
   5.2. Antibiotic Activity of Streptomycin-Phosphorylcholine Preparations
6. Example: Reduced Toxicity of Various Aminoglycoside Antibiotic-Ligand Preparations
7. Example: Amphotericin B Preparations
   7.1. Interaction of Amphotericin B with Water Soluble Cholesterol in Various Solvents
   7.2. Stability of Amphotericin B Preparations
   7.3. Reduced Toxicity of Amphotericin B Ligand Preparations
      7.3.1. Toxicity of PEG-Cholesterol
      7.3.2. Comparison of Toxicity of Amphotericin B and Amphotericin B/PEG-Cholesterol
      7.3.3. Toxicity of Various Amphotericin B Preparations in Mice
      7.3.4. Reduced Toxicity of Amphotericin B Preparations in Cell Culture
      7.3.5. Comparison of Hemolytic Properties of Amphotericin B Preparations

1. FIELD OF THE INVENTION

This invention relates to reducing or "buffering" the toxicity of drugs whose side effects are mediated through binding to endogenous cellular toxicity receptors, generally lipids. In particular, the drug is administered in combination with certain ligands such that the toxic effects of the drug are greatly reduced; however, the drug retains pharmacological activity.

2. BACKGROUND OF THE INVENTION

Several theories have been advanced to explain the mechanism by which a variety of toxic substances exert their desirable therapeutic and detrimental toxic effects in animals, including humans. Growing evidence suggests that these substances exert their effects by disturbing the cellular membranes (Schacht et al., 1983, "Aminoglycoside-cell Receptor Interactions: Implications for Toxicity and *In Vitro* Models," Thirteenth International Congress of Chemotherapy). More particularly, it is believed that the drugs bind to certain specific receptors which mediate the molecular activities responsible for their therapeutic and toxic effects in animals.

Theories of pharmacological action have been developed for the aminoglycoside antibiotics and for several other drugs, including the polyene and polyene macrolide antibiotics, a class of antifungal agents, as well as for adriamycin and cisplatin, known antineoplastic agents. These drugs, among others, exert their desirable therapeutic effects by binding to specific bacterial, fungal or tumor cellular receptors. Their undesirable toxic effects, on the other hand, are thought to be due to binding to specific toxicity receptors of non-drug target cells of the treated animal. Lipids have been suggested as toxicity receptors for these and other drugs.

Since theories have been more developed for the above-listed drugs, these will be discussed in greater detail below. It is to be understood, however, that drugs other than these may also exert their toxic effects through similar lipid-mediated mechanisms, and that the present invention encompasses all of such drugs.

2.1. THE AMINOGLYCOSIDE ANTIBIOTICS

The aminoglycoside antibiotics (e.g., streptomycin, gentamycin, kanamycin, tobramycin, etc.) are used almost exclusively to treat infections caused by bacteria. Their mode of bactericidal action involves inhibition of protein synthesis in susceptible microorganisms. Some susceptible microorganisms include Escherichia spp., Haemohilus spp., Listeria spp., Pseudomonas spp., Nocardia spp., Yersinia spp., Klebsiella spp., Enterobacter spp., Salmonella spp., Staphyloccocus spp., Streptococcus spp., Mycobacteria spp., Shigella spp., and Serratia spp., to name but a few.

The antibiotics in the aminoglycoside group all contain amino sugars in glycocidic linkages. They are polycations and their polarity is primarily responsible for the pharmacokinetic properties shared by the members of the group. For instance, these drugs are not adequately absorbed after oral administration, they do not easily penetrate the cerebrospinal fluid, and they are rapidly excreted by the kidney.

Serious toxicity is a major limitation to the usefulness of aminoglycosides. Three types of toxicity are often encountered with the use of aminoglycosides: (1) ototoxicity, which can involve both auditory and vestibular functions of the eighth cranial nerve; (2) nephrotoxicity, which is manifest as acute tubular damage; and (3) acute toxicity, which can follow intrapleural and intraperitoneal administration and is manifest as a neuromuscular blockade culminating in respiratory distress.

Ototoxicity involves labyrinthine dysfunction. Nearly 75% of patients given 2 g of streptomycin daily for 60 to 120 days manifest some vestibular disturbance; reduction of the dose to 1 g daily decreases the incidence to 25%. The effects occur in stages: (1) the acute stage (1 to 2 weeks) is characterized by nausea, vomiting and equilibratory difficulty including vertigo; (2) the acute state ends suddenly and is followed by chronic labyrinthitis characterized by ataxia; and (3) the chronic stage may persist for two months and is followed by a compensatory stage in which symptoms are latent and appear only when the eyes are closed. Full recovery of coordination may require 12 to 18 months, and some patients have permanent residual damage. There is no specific treatment for the vestibular deficiency.

In order to prevent or reduce the incidence and severity of the toxic effect on vestibular function, the aminoglycoside dose, the duration of therapy, and careful observation of the effects on the patient must be considered.

The toxic effect of aminoglycosides such as streptomycin and gentamycin is greater upon the vestibular than auditory component of the eighth cranial nerve, however, a decrease in hearing occurs in an appreciable number of patients (4–15% of individuals receiving the drug for more than 1 week) and, in rare cases, complete deafness can occur. Although the location of lesions responsible for vestibular and auditory dysfunction is disputed, it is believed that aminoglycosides destroy the ventral cochlear nuclei in the brain stem with extension of pathological changes to the terminals of the nerve fibers in the cochlea.

Nephrotoxicity caused by aminoglycosides is essentially a form of acute tubular necrosis and is initially manifested by the inability to concentrate urine. The very high concentrations of aminoglycoside antibiotics which accumulate in the renal cortex and urine correlate with the potential of these drugs to cause nephrotoxicity. For this reason, neomycin, the most nephrotoxic aminoglycoside, is not generally administered systemically in humans. Gentamycin seems to be the most nephrotoxic of the commonly used drugs.

Typically, after 5 to 7 days of aminoglycoside therapy, kidney damage, manifested by acute tubular necrosis and inability to concentrate urine, occurs and progresses as administration of the drug continues. At this stage, the urine contains protein and tubular cell casts. A reduction in glomerular filtration rate follows and is associated with elevation in the concentrations of the aminoglycoside, creatinine, and urea in plasma. Histopathology includes acute tubular damage with secondary interstitial damage. These changes are usually reversible and regeneration of renal cells occurs if the drug is discontinued.

Another serious effect of various aminoglycosides is the potentially fatal neuromuscular reaction which may develop when a drug such as streptomycin is instilled into the peritoneal cavity postoperatively (a practice in some surgical clinics). Acute muscular paralysis and difficulty in respiration may occur due to blockade of the neuromuscular junction by aminoglycosides. Neuromuscular blockade has also been observed in man following intravenous, intramuscular, and oral administration of these agents. The neuromuscular block may occur by inhibition of acetylcholine release from the preganglionic terminal (through competition with calcium ions) and perhaps to a lesser extent by stabilization of the post junctional membrane. The blockade is antagonized by calcium salts, but only inconsistently by anticholinesterase agents.

These neuromuscular reactions are shared to varying degrees by several other aminoglycoside antibiotics, particularly neomycin and kanamycin, and to a lesser extent by gentamycin, viomycin, paromomycin and tobramycin. Interestingly, the order of increasing ability of the aminoglycosides to affect acute toxic reactions seems to correlate with their ability to affect nephrotoxicity. That the underlying mechanism of these toxic reactions may be related is suggested by work associating the stimulation or depression of bioelectric events in nerve membranes with phosphoinositide metabolism (Hokin, 1969, Structure and Function of Nervous Tissue, Bourni, ed., Academic Press, New York, Vol. 3, pp. 161–184; Schact and Agranoff, 1972, J. Neurochem. 19:1417–1421; Margolis and Heller, 1966, J. Pharmacol. Expt. Ther. 74:307–312) and similar work associating phosphoinositide metabolism with aminoglycoside-induced ototoxicity and nephrotoxicity (Orsulakova et al., 1976, J. Neurochem. 26:285–290; Schibeci and Schacht, 1977, Biochem. Pharmacol. 26:1769–1774; Alexander et al., 1979, J. Antibiotics 32:504–510). Aminoglycoside antibiotics have been shown to bind to polyphosphoinositides in inner ear tissue and kidney in vivo. It has been postulated that phosphatidylinositol bisphosphates (phosphatidylinositol diphosphate) serve as in vivo receptors for aminoglycoside (hereinafter referred to as putative aminoglycoside toxicity receptors) and render tissues susceptible to these drugs (Lodhi et al., 1980, Biochem. Pharmacol. 29:597–601).

See "The Pharmacological Basis of Therapeutics," 6th edition, Goodman and Gilman, eds., 1980, Ch. 51, pp. 1162–1199, for a review of the aminoglycosides.

2.2. THE POLYENE AND POLYENE MACROLIDE ANTIBIOTICS

Polyene and macrolide antibiotics are a group of substances obtained from species of actinomycetes. For a review of the pharmacology of various polyene and polyene macrolide antibiotics, see "The Pharmacological Basis of Therapeutics", 6th edition, Goodman and Gilman, eds., 1980, pp. 1233–1236 and Medoff et al., 1983, Ann. Rev. Pharmacol. Toxicol. 23:303–330.

A large number and variety of untoward toxic effects may be associated with the use of these drugs. In particular, the toxic effects of amphotericin B include anaphylaxis, thrombopenia, flushing, generalized pain, convulsions, chills, fever, phlebitis, headache, anemia, anorexia, and decreased renal function. The toxic effects of the polyene and polyene macrolide antibiotics appear to result from binding to the toxicity receptor, cholesterol, a sterol present in animal cells but not fungal cells.

The polyene and polyene macrolide antibiotics appear to exert their therapeutic effects against fungi by binding to ergosterol, a sterol present in fungal cells but not in human cells. For example, amphotericin B binds in vitro to ergosterol with approximately ten times greater affinity than to cholesterol, the putative toxicity receptor. Bittman et al., 1982, Biochim. Biophys. Acta 685:219.

Encapsulating amphotericin B in liposomes has been suggested to attenuate the untoward effects of the drug. Taylor et al. (1982, Ann. Rev. Respir. Dis. 125:610–611) reported that liposome encapsulation significantly alters the drug's toxic effects. Their data indicates that encapsulation probably changes the tissue distribution of the drug. They observed reduced acute toxicity and a maximal tolerable dose nine times greater than the maximal tolerable dose for free amphotericin B. Liposome encapsulation of amphotericin B also prolongs the survival of mice infected with *Histoplasma capsulatum*. New et al., (1981, J. Antimicrob. Chemother. 8:371–381) have used amphotericin B with cholesterol for the purpose of treating leishmaniasis. Increased effectiveness of the drug was observed.

Sodium deoxycholate is used in a commercial preparation, Fungizone, to effect a colloidal dispersion of amphotericin B, buffers and diluents. Fungizone is available packaged in vials as a sterile, lyophilized powder to which water is added. This mixture is shaken and added to a 5% dextrose solution. The resulting solution can then be administered as an injection.

2.3. ADRIAMYCIN

Adriamycin, an antineoplastic drug, is a glycosidic anthracycline antibiotic that is a fermentation product of the fungus *Streptomyces peucetius* var. *caesius*. Adriamycin has a tetracycline ring structure with an unusual sugar, daunosamine, attached by a glycosidic linkage.

Adriamycin is effective in the treatment of acute leukemias and malignant lymphomas and in a number of solid tumors. The drug is particularly beneficial in a wide range of sarcomas, including osteogenic, Ewing's, and soft-tissue sarcomas. It is one of the most active single agents for the treatment of metastatic adenocarcinoma of the breast, carcinoma of the bladder, bronchogenic carcinoma and neuroblastoma.

Myelosuppression is a major dose-limiting complication with adriamycin. Stomatitis, gastrointestinal disturbances, and alopecia are common but reversible. Cardiomyopathy is a unique characteristic of the anthracycline antibiotics. Tachycardia, arrhythmias, and ST-T wave changes in the ECG may be early manifestations of cardiac toxicity. Severe and rapidly progressive congestive heart failure may follow. Nonspecific alterations, including a decrease in the number of myocardial fibrils, mitochondrial changes, and cellular degeneration, are visible by electron microscopy. In view of this cardiotoxicty, therapeutic utility of adriamycin is limited.

Because adriamycin is primarily metabolized and excreted by the liver, it is important to reduce the dosage in patients with impaired hepatic funtion.

The antitumor effects of adriamycin appear to result from intercalation of the molecule between adjacent base pairs of DNA, thus interfering with the proliferation of rapidly dividing tumor cells. Toxic effects appear to be mediated by binding of the drug to cardiolipin, the putative toxicity receptor. Goormaghtigh et al., have shown that adriamycin adsorbs in vitro to cardiolipin and, to lesser degrees, to phosphatidylserine and phosphatidic acid (1980, Biochem. Pharmacol. 29:3003-3010). There appears to be a relatively strong electrostatic interaction between protonated amine groups of the sugar residues of adriamycin and ionized phosphate residues of the cardiolipin, concomitant with interaction between adjacent anthraquinone chromophores. The association constant for cardiolipin/adriamycin is about $1.6 \times 10^6$ mol$^{-1}$, while the association constant for DNA/adriamycin is about $2.4 \times 10^6$ mol$^{-1}$. Thus, adriamycin has a higher affinity for DNA than for cardiolipin.

Fluorescent studies have revealed that adriamycin binds to the head group of cardiolipin. Goormaghtigh et al., 1980, Biochim. Biophys. Acta 597:1-14.

Goormaghtigh et al., also observed a good correlation between binding of adriamycin derivatives to cardiolipin and mitochondrial toxicity (1980, Biochem. Pharmacol. 29:3003-3010). Thus, it has been proposed that cardiolipin is the toxicity receptor for adriamycin in animals (Goormaghtigh et al., 1982, Biochem. Biophys. Res. Comm. 104:314-320).

It has been proposed to encapsulate adriamycin in liposomes (Forssen and Tokes, 1983, Cancer Res. 43:546-550). Liposome encapsulation changes the tissue distribution of adriamycin; the free drug appears predominantly in the liver and spleen. There is an apparent reduction in chronic cardiotoxicity and an increase in antileukemic activity.

2.4. CLISPLATIN

Cisplatin is an inorganic, water soluble, platinum containing coordination complex (planar), containing ammonium and chloride residues in the cis configuration. Despite pronounced nephrotoxicity and ototoxicity, cisplatin is very useful in combination chemotherapy of metastatic, testicular and ovarian carcinoma. Encouraging effects have also been reported during treatment of tumors of the bladder and of the head and neck.

For a review of the pharmacology of cisplatin, see "The Pharmacological Basis of Therapeutics", 6th edition, Goodman and Gilman, eds., 1980, pp. 1298-1299.

Studies on crystal structure analysis of cisplatin have demonstrated a strong binding of these compounds to guanosine and related inosine derivatives (e.g., inosine 5'-monophosphate) (Louie and Bau, 1977, J. Amer. Chem. Soc. 99:3874-3876; Goodgame et al., 1975, Biochim. Biophys. Acta 378:153; Bau et al., 1977, J. Clin. Hematol. Oncol., Wadley Medical Bulletin 7:51). Thus, the mechanism of action leading to the nephrotoxicity and ototoxicity observed upon administration of cisplatin may be similar to that for the aminoglycoside antibiotics (see Section 2.1.) and ligands useful for buffering aminoglycosides may be used for buffering cisplatin.

2.5. CONCURRENT THERAPY

Combinations of antimicrobial agents have been widely described for the treatment of infections. In fact, combination therapy using a number of different drugs is recommended for the treatment of many cancers.

Concurrent therapy, however, with certain pharmaceutical agents may be complicated because agents which exert a synergistic effect in vitro cannot be formulated in a single mixture to use in vitro. Mixtures of gentamycin and nafcillin, a penicillin, at therapeutically effective concentrations result in the formation of complexes that precipitate out of solution and, therefore, cannot be administered in vivo together. In fact, certain drug combinations are not recommended for use in vivo due to drug incompatibility (i.e., either inactivation of the drug or formation of a precipitate). For example, it is recommended that the following antibiotics not be mixed with any other drug: gentamycin, kanamycin, lincomycin, cephalothin, and ampicillin (Davis and Abbitt, 1977, JAVMA 170(2):204-207). Moreover, certain agents cannot be solubilized in the same media due to chemical restraints (e.g., a lipid soluble compound and a water soluble compound).

3. SUMMARY OF THE INVENTION

The present invention relates to preparations of certain drugs in admixture with various ligands that reduce the toxicity of the drugs in vivo. When these drugs are administered in combination with the ligands described herein, toxicity of the drug is greatly reduced while the drug retains pharmacological activity. Drugs whose toxic effects may be reduced or "buffered" by the method of the invention include those in which toxic side effects are mediated through binding to endogenous cellular substrates, which are generally lipids. The term "ligand" as used herein includes compounds which reduce the toxicity of the drugs in the preparation; the term is not meant to indicate the type of interaction or reaction between such compounds and the drug.

A particularly useful advantage of the drug-ligand preparations described herein is that high doses of drug may be administered to an animal or human with lessened deleterious toxic effects than observed with conventional drug preparations. Thus, maintenance doses may be given less often to achieve acceptable serum levels. Since higher doses of drug may be administered without the usual toxic effects, the preparations of the invention allow for a greater margin of error in selection of initial doses of drug.

The preparations of the invention can be viewed as an entirely new class of therapeutic compositions possessing all of the advantages of the conventional drug preparations with reduction of the major clinically relevant disadvantages.

4. DETAILED DESCRIPTION OF THE INVENTION

The present invention involves drug preparations of reduced toxicity. A drug-ligand preparation is made such that, when administered to an animal or human, the toxicity of the drug in the preparation is reduced or eliminated, yet the drug retains pharmacological activity.

The ligand to be used in the preparations of the invention depends on the particular drug used and the relevant toxicity receptor. Generally, the drugs which may be used in practicing the present invention are those whose in vivo toxicity to mammalian cells is mediated through binding to lipid toxicity receptors. Such drugs include monoaminated or polyaminated drugs, antimicrobials, antivirals, antifungals, antibacterials, aminoglycosides, polyene and polyene macrolide antibiotics, lincosamides, and polymixins, to name a few.

According to the invention, appropriate ligands (lipids or lipid head groups) to which the drug binds are admixed with the drug prior to administration. It is believed the ligand binds to the toxicity receptor to prevent interaction between the drug and the receptor. This combination of drug with ligand prevents or reduces the binding of the drug to its endogenous toxicity receptor, thus reducing or eliminating the toxicity of the drug. The drug retains its pharmacological effectiveness.

4.1. AMINOGLYCOSIDE-LIGAND PREPARATIONS

As discussed in Section 2.1., it is believed that phosphatidylinositol bisphosphates serve as in vivo toxicity receptors for the aminoglycoside antibiotics. According to the invention, aminoglycosides are mixed with ligands which prevent or reduce the binding of aminoglycosides to the endogenous toxicity receptors. Ligands useful in the aminoglycoside preparations of the invention include, but are not limited to, certain phosphate esters, phosphate anhydrides and sulfatides.

The ligands which may be used in the present invention are not equally effective in reducing aminoglycoside toxicity (see Section 5.1., infra). The ability of these ligands to reduce toxicity of aminoglycoside antibiotics appears to correlate with two phenomena. The first phenomenon is the degree to which various ligands appear to associate with the aminoglycosides by virtue of the strength of dipole-dipole interaction and subsequent hydrogen bonding. Ligands exhibiting extensive resonance structures, whereby electron delocalization is easily visualized, seem to provide the most protection against aminoglycoside toxicity. Ligands exhibiting lower potential for hydrogen bonding provide only intermediate protection. The configuration of negative charges on phosphatidylinositol bisphosphate (the putative aminoglycoside toxicity receptor) allow for a specific, three point binding to positively charged aminoglycosides. Although a strong correlation exists between the charge of aminoglycosides and their relative toxicity (Schact, 1983, Proceedings of the Thirteenth International Congress of Chemotherapy), some aminoglycosides do not fit this pattern of charge versus toxicity and, thus may be stabilized in their binding to phosphatidylinositol bisphosphate by hydrogen bonding. Thus, the ligands that most effectively reduce the toxicity seem to have the same binding characteristics of phosphatidylinositol bisphosphate.

The second phenomenon concerning the efficacy of various ligands to reduce aminoglycoside toxicity concerns a correlation of the ability of these ligands to bind C-reactive protein. C-reactive protein is an acute phase protein appearing in the serum of man during various pathologic conditions. It is precipitated from such serum by pneumococcal C-polysaccharide in the presence of calcium ions. Phosphorylcholine and lysophosphatidylcholine bind strongly to C-reactive protein, while phosphorylethanolamine and glycerolphosphorylcholine bind less strongly (Volanakis and Kaplan, 1970, Proc. Soc. Exp. Biol. Med. 136:612-614). Coincidentally, phosphorylcholine and lysophosphatidylcholine are very effective in reducing aminoglycoside toxicity whereas phosphorylethanolamine and glycerolphosphorylcholine are less effective. The correlation of the ability of these ligands to bind C-reactive protein and the ability to reduce aminoglycoside toxicity while retaining antimicrobial activity remains unexplained. This correlation is useful as a predictive tool to select candidates for ligands useful in the preparations of the invention, but it is to be understood that this does not necessarily indicate the mechanism of action by which the preparations of the invention exert the observed effects.

The ligands which are used in the present invention to attenuate aminoglycoside toxicity include, but are not limited to: lysophosphatidylcholine, phosphorylcholine, tripolyphosphate, phosphorylserine, phosphoglyceric acid, inositol monophosphate, inositol biphosphate, inositol triphosphate, inositol tetraphosphate, inositol pentaphosphate, inositol hexaphosphate, and phosphorylinositols; i.e., phosphate esters and phosphate anhydrides. In addition, lipoteichoic acids, teichoic acids (including pneumococcal and streptococcal C-polysaccharide), sulfatides, nucleotides, stearylamines, diacylglycerol, aminocaproic acid, pyridoxal phosphate, chondroiton sulfate, cysteic acid, p-aminophenyl phosphate, p-aminophenyl sulfate, poly-1-lysine, poly-1-arginine, poly-1-glutamic acid, poly-1-aspartic acid and other polymeric and monomeric amino acids will efficaciously reduce toxicity.

Further, phospholipids such as cardiolipin, phosphatidylinositolphosphates, including phosphatidylinositol phosphate and phosphatidylinositol diphosphate, phosphatidylcholine, phosphatidylserine, phosphatidylglycerol, galactocerebroside sulfate, phosphatidylinositol and phosphatidic acid, all of which will spontaneously form liposomes at excess concentrations in water (above their critical micelle concentrations) would also be expected to reduce aminoglycoside toxicity. Such aminoglycoside-containing liposomes would allow aminoglycosides to be given safely above the $LD_{10}$ or $LD_{50}$ of the free drug. For example, the $LD_{50}$ of streptomycin in mice is 741 mg/kg (see Table IV infra); encapsulation of streptomycin in liposomes would allow the administration of this concentration of streptomycin without observing any acute toxicity.

In a particular embodiment, the phospholipids phosphatidylinositol phosphate and phosphatidylinositol bisphosphate may be especially useful when used at concentrations greater than their critical micelle concentrations; that is, with the aminoglycoside antibiotic encapsulated within liposomes of these phospholipids. As discussed above, these phospholipids are the putative toxicity receptors for aminoglycosides, and for this reason, they are especially desirable for use as ligands in the preparations of the invention, either above or below their critical micelle concentrations (i.e., in liposomes or in solution).

The preparations of the invention may be used in situations requiring high initial concentrations and/or high levels of sustained antibiotic therapy. They may also be useful in renal compromised patients in which initial toxicity to the patient is a concern. The invention also enables administration of antibiotics at levels higher than currently acceptable levels for sustained minimal inhibitory serum concentrations. By virtue of the ability to administer higher loading dosages of antibiotics, higher sustained levels of antibiotics are possible. The technology of the invention may also be applied in veterinary therapy to situations including, but not limited to, gram-negative enteritis, mastitis, "shipping fever", infectious keratoconjunctivitis, vibrosis, mycobacterial infections and Brucella spp. infections.

The aminoglycoside antibiotics which may be used in the present invention include but are not limited to: streptomycin, gentamycin, tobramycin, amikacin, kanamycin and neomycin.

According to the present invention, an aminoglycoside antibiotic is mixed with a ligand prior to administration to an organism in vivo. Sterile water is the preferred diluent. Due to the nature of the aminoglycoside antibiotics, parenteral administration of the preparation is the preferred route. The aminoglycoside and ligand may be mixed immediately prior to administration in vivo. Alternatively, the aminoglycoside and ligand may be mixed for 1 hour, 2 hours, or longer prior to administration, depending on the stability of the aminoglycoside. Using either method, toxicity is reduced and the antibiotic retains antimicrobial activity. As a result, increased doses of antibiotic may be administered to animals or humans with greater safety.

The reasons for the attenuation of toxicity remain obscure, and a number of mechanisms seem plausible. Possibly the ligands form a complex with the aminoglycosides, thus preventing the binding of the antibiotic to its putative aminoglycoside toxicity receptor in vivo. It is also conceivable that association between aminoglycosides and ligands occurs by virtue of dipole interactions, resulting in an array of hydrogen bonds between them. At physiological pH, the guanidino groups of aminoglycosides are fully protonated and are stabilized by resonance. These groups are particularly good sites for hydrogen bond interactions with phosphate groups (examples of which are the binding of $NAD^+$ to arginine 101 of lactate dehydrogenase or the binding of thymidine 3'-5' diphosphate to the guanidinian ions of arginines 35 and 87 of staphylococcal nuclease). Guanidino groups are capable of forming up to five hydrogen bonds each, and can interact simultaneously with phosphate groups and adjacent groups such as carbonyls. Alternatively, the ligands may bind to the putative aminoglycoside toxicity receptors themselves, thus preventing the binding of the antibiotic.

4.1.1. EVIDENCE FOR COMPLEX FORMATION

The following observations and data suggest that an aminoglycoside-ligand complex is formed which is less toxic than the aminoglycoside alone:

(1) SDS-Polyacrylamide Gel Electrophoresis: Equal volumes of mouse serum were incubated for 0.5 hour and 2 hours with $^{125}$I-gentamycin sulfate ($^{125}$I-GS) or with $^{125}$I-gentamycin-phosphorylcholine ($^{125}$I-GPC), 1:3 molar ratio, at $1 \times 10^5$ cpm per sample. Aliquots of the incubated serum samples and aliquots of $^{125}$I-GS as well as $^{125}$I-GPC were then prepared for sodium dodecyl sulfate polyacrylamide gel electrophoresis (SDS-PAGE) by boiling the samples in $\beta$-mercaptoethanol ($\beta$-ME), SDS, and urea for 1 to 2 minutes as described by Laemmali (1970, Nature 227:680). After electrophoresis the gel was stained with Coomassie-Blue (C-Blue) and exposed to X-ray film (autoradiographed) at $-70°$ C. In the lane representing the serum sample incubated with $^{125}$I-GS and in the lane representing the serum sample incubated with $^{125}$I-GPC all serum polypeptides were stained with C-Blue but none of the serum polypeptide bands were radioactively labeled. However, in the lane representing the serum sample sample incubated with $^{125}$I-GPC a low molecular weight band (i.e., lower than the molecular weights of the serum polypeptides) stained intensely with C-Blue; this band was also radioactive as determined by autoradiography. This low molecular weight band was not present in the lane representing serum incubated with $^{125}$I-GS. In the lane representing $^{125}$I-GS (without sera) no bands were detected by autoradiography, but in the lane representing $^{125}$I-GPC (without sera) the same low molecular weight, radioactively-labeled band which stained with C-Blue was detected.

Since phosphorylcholine stains intensely with C-Blue, this low molecular weight band which is stained by C-Blue and is also radioactively labeled represents the putative $^{125}$I-gentamycin-phosphorylcholine complex. Interestingly, the putative complex did not dissociate under the denaturing conditions used in the sample preparation for SDS-PAGE.

(2) Dissociation of the Putative Complex: If the aminoglycoside-ligand mixture is prepared or administered in an appropriate "high-salt" solution (a high salt concentration has been shown to inhibit formation of complexes or cause dissociation of some complexes), the toxicity of the aminoglycoside is not reduced. One explanation for this observation is that dispersing the aminoglycoside-ligand mixture in 0.6M ammonium acetate dissociates the complex formed between the aminoglycoside and the ligand. In support of this, see Schact, 1978, J. Lipid Res. 19:1603–1607, where 0.6M ammonium acetate is reported to elute phosphatidylinositol phosphate which was bound to neomycin immobilized on a column. When an aminoglycoside-ligand preparation dispersed in 0.6M ammonium acetate is administered subcutaneously to mice, it appears that toxicity is not significantly reduced (see Table I).

(3) Separate Administration of Ligand and Aminoglycoside: If the ligand is administered to an animal before the the aminoglycoside is administered, the toxicity of the aminoglycoside is not reduced to the same extent that a mixture of streptomycin and phosphorylcholine reduces toxicity (see Table I).

TABLE I
COMPARISON OF TOXICITY OF STREPTOMYCIN ADMINISTERED WITH AND WITHOUT LIGAND

| Treatment[1] | Lethality No. Dead/No. Inoculated | Percent Lethality |
|---|---|---|
| Control Streptomycin | 7/8 | 87.5 |
| Aminoglycoside + Ligand[2] (Streptomycin + Phosphorylcholine) | 1/8, 0/6 | 7 |
| Aminoglycoside + Ligand in Ammonium Acetate Buffer[3] (Streptomycin + Phosphorylcholine) | 3/6 | 50 |
| Aminoglycoside Administered After Inoculation of Ligand[4] (Min. post-inoculation) | | |
| 0 | 5/8 | 62.5 |
| 10 | 5/8 | 62.5 |
| 30 | 6/7 | 85.7 |

[1]In all trials the streptomycin dose was 1000 mg/kg body weight inoculated subcutaneously in Swiss Webster mice. In all trials where ligand was administered, the molar ratio of aminoglycoside to ligand was 1:3.
[2]The aminoglycoside + ligand mixture was prepared by mixing streptomycin and phosphorylcholine immediately prior to administration.
[3]The streptomycin + phosphorylcholine mixture was prepared in 0.6M ammonium acetate. Subcutaneous injection of ammonium acetate alone (0.6M) was not lethal (0/6 lethality).
[4]In this trial both the phosphorylcholine and streptomycin were inoculated subcutaneously at different sites after the time spans indicated.

It appears that reduction in aminoglycoside toxicity is related to the formation of a complex between the aminoglycoside and ligand for the following reasons: (1) drug toxicity is not significantly reduced when the aminoglycoside and ligand are administered in ammonium acetate (at concentrations which are known to dissociate or prevent formation of some complexes); and (2) separate administrations of the ligand followed by drug were not effective in reducing toxicity of the streptomycin. However, the invention is not to be limited to this theory of interaction between the aminoglycoside and ligand. Other potential explanations for the observed reduction in toxicity are discussed above.

4.2. POLYENE AND POLYENE MACROLIDE ANTIBIOTIC-LIGAND PREPARATIONS

As described in Section 2.2., the polyene and polyene macrolide antibiotics are believed to exert their toxic effects in humans and animals by binding to cholesterol, the putative toxicity receptor. Thus, ligands suitable for reducing the toxicity in mammals of the polyene and polyene macrolide antibiotics, such as amphotericin B, are those which prevent binding to endogenous cholesterol. Such ligands would include sterols and water soluble derivatives thereof, and, in particular, cholesterol and its water soluble derivatives such as polyethylene glycol-cholesterol (PEG-cholesterol), cholesterol hemisuccinate (CHS), and the like. The water soluble cholesterol derivatives are of particular utility since clear solutions are highly preferred for injection.

The lipid ligands of this particular embodiment of the present invention may be prepared at a concentration below that used for micelle formation and are thus free of liposomes. Since liposomes are not present, there is no difficulty with respect to stability of the preparations. Furthermore, administration of cholesterol-containing liposomes could result in the deposition of the liposomes primarily in the liver and spleen, which may be undesirable. Additionally, one need not be concerned about administering a particulate preparation which may clog or reduce circulation. Thus, effective preparations of polyene or polyene macrolide antibiotics mixed with water soluble cholesterol or a cholesterol derivative, yet free of liposomes, are highly effective in reducing toxicity of the drugs.

Amphotericin B, a polyene antibiotic, is not soluble in water and, for injections, is commercially solubilized in sodium deoxycholate which also has toxic properties (Fungizone, E. R. Squibb & Sons, Princeton, N.J.). Consequently, because of the two toxic components of the commercial pharmaceutical agent, therapeutic doses of Fungizone or amphotericin B-deoxycholate (amphotericin B-DOC) must be kept low. As will be seen in the examples following, both a reduction in toxicity and solubilization of Amphotericin B can be obtained by solubilizing the amphotericin B in a water soluble cholesterol preparation. Reduction in toxicity of an amphotericin B administration is obtained in two ways:

(1) Introduction into the system of toxic deoxycholate is eliminated since non-toxic water soluble cholesterol is used as the solubilizer; and (2) Water soluble cholesterol, when added to amphotericin B, blocks affinity for in situ lipid binding sites on the drug, thus blocking the toxicity pathway.

4.2.1. EVIDENCE FOR COMPLEX FORMATION

As indicated in Section 4.1., the reasons for the attenuation of toxicity seen when polyene or polyene macrolide antibiotics are administered in combination with the ligands of the present invention remain obscure. One possbility is that the ligand forms a complex with the polyene antibiotic thus preventing binding of the drug to its putative toxicity receptor.

The following observations and data suggest that such a complex is formed between amphotericin B and the ligand PEG-cholesterol.

Spectrophotometric Analysis: The absorbance spectrum of amphotericin B in water demonstrates three peaks at the following wavelengths: 386, 407, 418 nm. When Fungizone is mixed with PEG-cholesterol in an aqueous solution, the peak at 407 nm disappears. The absence of an absorption peak at about 407 nm is evidence of the amphotericin B-cholesterol complex formation. However, the absorbance spectra of Fungizone in methanol and Fungizone mixed with PEG-cholesterol in methanol are identical. This indicates that no complex is formed in methanol (See Section 7 for details).

4.3. ADRIAMYCIN-LIGAND PREPARATIONS

The cardiotoxicity of adriamycin appears to be mediated by binding of the drug to cardiolipin or cardiolipin head groups (see Section 2.3.). Accordingly, these preparations of the present invention utilize adriamycin in admixture with ligands which block the binding of adriamycin to endogenous cardiolipin. Such ligands would include cardiolipin or cardiolipin head groups.

As with the polyene and polyene macrolide-ligand preparations of Section 4.2., the preparations of the invention do not contain liposomes. Hence, none of the disadvantages of liposome administration are encountered with the preparations of the invention.

4.4. CISPLATIN-LIGAND PREPARATIONS

The nephrotoxicity and ototoxicity of cisplatin are apparently mediated in a similar fashion to that of the aminoglycoside antibiotics (see Section 2.4.). Consequently, any ligand which interferes with the binding of cisplatin to phosphatidylinositol bisphosphate is suitable for buffering toxicity of cisplatin.

5. EXAMPLES: STREPTOMYCIN PREPARATIONS

The data presented in the following examples demonstrate the reduction of toxicity of aminoglycoside antiobiotics which retain antimicrobial activity when administered as an aminoglycoside-ligand preparation.

5.1. REDUCED TOXICITY OF STREPTOMYCIN-LIGAND PREPARATIONS

The following data (presented in Table II) compare the acute toxicity of streptomycin administered subcutaneously in mice to that of streptomycin administered in combination with various ligands.

For each trial 200 mg of streptomycin sulfate and one of the following ligands was dissolved in distilled water (final volume 5 ml) to obtain a 1:3 molar ratio or a 1:1 molar ratio of streptomycin to ligand: 260 mg egg lysophosphatidylcholine (1:3); 87 mg egg lysophosphatidylcholine (1:1); 129 mg phosphorylcholine (1:3); 110 mg inositol hexaphosphate (1:1); 80 mg tripolyphosphate (1:1); 71 mg phosphorylethanolamine (1:3); 70 mg choline chloride (1:3); 93 mg phosphorylserine (1:3); 196 mg inosine 5'-monophosphate (1:3); 115 mg phosphoglyceric acid (1:3); or 76.5 mg inositol monophosphate (1:1). These solutions were mixed for at least one hour. Once dissolved, a 0.6 ml aliquot of the solution was administered subcutaneously into mice (average weight of 24 gm each) in order to deliver a dose of 1000 mg streptomycin per kg body weight.

The results in Table II clearly demonstrate that egg lysophosphatidylcholine, phosphorylcholine and inositol hexaphosphate are very effective in reducing the toxicity of streptomycin. The remaining ligands included in Table II vary in their effectiveness in reducing aminoglycoside toxicity.

TABLE II

COMPARISON OF THE ACUTE TOXICITY OF STREPTOMYCIN ADMINISTERED WITH AND WITHOUT VARIOUS LIGANDS[1]

| | Molar Ratio Streptomycin: Ligand | Lethality No. Dead/ No. Inoculated | Percent Lethality |
|---|---|---|---|
| Control Streptomycin | | 6/8, 5/6, 6/8 | 77.7 |
| Ligand[2] | | | |
| Egg Lysophosphatidylchloine | (1:3) | 0/8, 0/4 | 0 |
| Egg Lysophosphatidylcholine | (1:1) | 0/7 | 0 |
| Phosphorylcholine | (1:3) | 0/8, 0/8 | 0 |
| Inositol hexaphosphate | (1:1) | 0/8 | 0 |
| Phosphoglyceric acid | (1:3) | 3/8 | 37.5 |
| Tripolyphosphate | (1:1) | 3/8, 4/7 | 47.3 |
| Phosphorylserine | (1:3) | 4/8 | 50 |
| Inositol monophosphate | (1:1) | 5/8 | 62.5 |
| Phosphorylethanolamine[3] | (1:3) | 4/7 | 66 |
| Inosine 5'-monophosphate | (1:3) | 7/8 | 87.5 |
| Choline chloride[4] | (1:3) | 7/7 | 100 |

[1] In all trials the streptomycin dose was 1000 mg/kg body weight, inoculated subcutaneously in Swiss Webster mice.
[2] The following compounds, when mixed with the aminoglycoside, precipitated out of solution and could not be administered to mice: egg phosphatidic acid and inositol hexasulfate.
[3] Phosphorylethanolamine administered without streptomycin was not lethal (0/7 lethality).
[4] Choline chloride administered without streptomycin was not lethal (0/8 lethality).

5.2. ANTIBIOTIC ACTIVITY OF STREPTOMYCINPHOSPHORYLCHOLINE PREPARATIONS

The following experiment compares the antibiotic activity of sera from mice inoculated subcutaneously with streptomycin to that of sera from mice inoculated with a streptomycin-phosphorylcholine preparation. The results demonstrate that the toxicity of streptomycin can be reduced (See Table II) while retaining antimicrobial activity (See Table III).

Adult Swiss Webster mice were inoculated subcutaneously with 0.6 ml of either streptomycin at a concentration of 18.3 mg/ml (400 mg/kg body weight) or a phosphorylcholine-streptomycin preparation (antibiotic as above and phosphorylcholine 11.5 mg/ml, i.e., 255 mg/kg body weight). At 2, 4, 6, 8.5 and 19 hours post-inoculation, three mice from each group were anesthetized with ether and the retro-orbital blood was collected individually using heparinized capillary pipets. After the last bleeding, the blood was centrifuged to separate serum from cells. The antibiotic activity of the sera was determined in 96-well, U-shaped microplates as follows.

Each serum sample (50 $\mu$l) was mixed with 50 $\mu$l tryptosephosphate broth. These were serially diluted in the microplate wells (50 $\mu$l aliquots were diluted into 50 $\mu$l of broth serially). Then, 50 $\mu$l of broth containing $10^3$ colony-forming units of *Staphylococcus aureus* (ATCC No. 14154) were added to each well and the microplates were incubated overnight at 37° C. The endpoint of the titration was indicated by that dilution of serum in which the growth of *S. aureus* in micro-well culture was inhibited approximately 50% as compared to the control cultures which received no antibiotics.

The results (Table III) indicate that antimicrobial activity of mouse sera obtained at different time intervals post-inoculation with antibiotic is similar regardless of whether streptomycin was administered alone or in combination with phosphorylcholine. Therefore, the antibiotic retains antimicrobial activity.

TABLE III

ANTIBACTERIAL ACTIVITY OF SERA FROM MICE INOCULATED SUBCUTANEOUSLY WITH STREPTOMYCIN-PHOSPHORYLCHOLINE PREPARATIONS

| Hours Post Inoculation | Titer[1] in Individual Sera of Mice Inoculated with: | |
|---|---|---|
| | Streptomycin + Phosphorylcholine | Streptomycin |
| 2 | 2, 2, 2 | 2, 2, 2 |
| 4 | 4, 4, 4 | 4, 4, 4 |
| 6 | 8, 8, 8 | 8, 8, 8–16 |
| 8.5 | 2–4, 2–4, 2 | 2, 2, 2 |
| 19 | 2, 2, 2 | 0, 0, 2 |

[1]Reciprocal of the end-point dilution in the micro-assay described in text.

6. EXAMPLE: REDUCED TOXICITY OF VARIOUS AMINOGLYCOSIDE ANTIBIOTIC-PHOSPHORYLCHOLINE PREPARATIONS

The following data compares the $LD_{50}$ of various aminoglycoside antibiotics administered with and without ligand.

In order to determined the $LD_{50}$ of the aminoglycoside preparations a quantity of antibiotic was dissolved in 20 ml distilled water with or without phosphorylcholine to achieve a final 1:3 molar ratio of antibiotic to ligand. Then, 0.6 ml aliquots of serial dilutions of the aminoglycoside preparations were injected subcutaneously into Swiss Webster mice (ten animals per group, average weight 23 g each). After 24 hours the number of survivors in each group was determined and the $LD_{50}$ and 95% confidence limits for each were computed according to the Spearman-Karber Method for Quantal Data (from Finney, 1952, Statistical Method in Biological Assay, Hafner Pub. Co., New York). Results are shown in Table IV.

The results in Table IV clearly demonstrate that the $LD_{50}$ of each antibiotic administered in conjunction with ligand is greater than the $LD_{50}$ of the same antibiotic administered alone.

TABLE IV

$LD_{50}$ OF AMINOGLYCOSIDE ANTIBIOTICS ADMINISTERED WITH AND WITHOUT PHOSPHORYLCHOLINE

| Aminoglycoside[1] Preparation | $LD_{50}$[2] (mg/kg) | 95% Confidence Interval[3] (mg/kg) | $LD_{50}$[4] Ratio |
|---|---|---|---|
| Streptomycin | 741 | 616–891 | — |
| Streptomycin + Phosphorylcholine (1:3) | 2123 | 1725–2570 | 1:2.9 |
| Gentamycin | 692 | 602–794 | — |
| Gentamycin + Phosphorylcholine (1:3) | 1202 | 959–1506 | 1:1.7 |
| Neomycin | 371 | 301–457 | — |
| Neomycin + Phosphorylcholine (1:3) | 912 | 758–1096 | 1:2.5 |

[1]See text for explanation of subcutaneous administration of aminoglycoside preparations in Swiss Webster mice.
[2]The $LD_{50}$ is expressed as mg aminoglycoside antibiotic per kg body weight.
[3]Ten animals were inoculated in each group.
[4]The $LD_{50}$ ratio is the ratio of the $LD_{50}$ of the aminoglycoside antibiotic to the $LD_{50}$ of the aminoglycoside-ligand preparation.

7. EXAMPLES: AMPHOTERICIN B PREPARATIONS

The following subsections described the preparation and the formation of a complex (as evidenced by spectrophotometric data) between amphotericin B (AmB) a polyene macrolide antibiotic and PEG-cholesterol. The complex appears to remain stable in vivo. Furthermore, the complex has a reduced toxic effect on cells in vitro and when used in vivo.

7.1. INTERACTION OF AMPHOTERICIN B WITH PEG-CHOLESTEROL IN VARIOUS SOLVENTS

Because amphotericin B is insoluble in aqueous solutions, dimethysulfoxide (DMSO) is used to solubilize the amphotericin B. The addition of PEG-cholesterol to the solubilized amphotericin B results in the formation of a complex between the amphotericin B and the PEG-cholesterol. However, DMSO, which is not approved for internal use in humans, cannot be removed by rotoevaporation. Therefore an alternate means of removal must be used. When methanol is added to the preparation, the methanol forms an easily removable azeotrope with DMSO. When PEG-cholesterol is added concurrently with the methanol, maximum complex formation is achieved.

Preparation 1: 25 mg of amphotericin B (AmB) was dissolved in 2.0 ml of DMSO. Then 30 mg PEG-cholesterol and 23 ml methanol were added to the dissolved amphotericin B. With time a precipitate formed which was removed by centrifugation at 10,000×g for 10 minutes. The resulting supernatant was rotoevaporated to dryness at 55° C.–60° C. The remaining film was suspended in 10 ml distilled water and sonicated to clearness. This preparation was designated AmB (25)/PEG-Chol.

Preparation 2: Preparation 2 was prepared identically as for Preparation 1 except that 150 mg PEG-cholesterol was used. The preparation was designated AmB(150)/PEG-Chol-2.

Absorbance spectra at a wavelength of 350–550 nm were obtained for the following solutions: (1) Fungizone (a commercially available preparation consisting of a lyophilized powder of amphotericin B and sodium deoxycholate) in either methanol or water; and (2) AmB(25)/PEG-Chol and AmB(150)/PEG-Chol in either water or methanol. The spectrum obtained for Fungizone in water consisted of peaks at about 386, 407 and 418 nm. The spectra obtained for both AmB/PEG-Chol preparations in water consisted of peaks at about 387 and 417 nm; the absence of an absorption peak at about 407 nm in the spectrum is evidence of an interaction or complex formation between Amphotericin B and PEG-cholesterol. This is further supported by the fact that the spectra obtained for Fungizone in methanol and AmB/PEG-Chol in methanol are identical. The identical spectra indicates that, in methanol, amphotericin B does not form a complex with PEG-cholesterol.

7.2. STABILITY OF AMPHOTERICIN B/PEG CHOLESTEROL

A sample of 5 mg of AmB was dissolved in 0.5 ml of DMSO. To this was added 10 mg of PEG-cholesterol and 3.0 ml methanol. This solution was centrifuged at 12,100×g for 10 minutes to remove a small amount of flocculate, rotoevaporated to dryness, resuspended in 10 ml distilled water adjusted to approximately pH 7.0, and sonicated to clearness. The resulting clear solution containing the AmB/PEG-cholesterol was divided into two equal aliquots (A and B).

The following experiment indicates that the removal of PEG-cholesterol results in a loss of stability of the complex: CHCl$_3$ was added dropwise to aliquot A. The CHCl$_3$ acted to dissolve or extract the PEG-cholesterol resulting in a precipitation of amphotericin B in the aqueous phase. DMSO, when added dropwise to the precipitate, dissolved the amphotericin B in the aqueous phase.

In order to use the AmB/PEG-cholesterol complexes in vivo, it is important that the complex remain soluble in aqueous environments. To ensure that no precipitation of amphotericin B would occur in an aqueous environment, aliquot B was added dropwise to a 5% dextrose solution which is similar to plasma in osmolality. No precipitate resulted.

For purpose of comparison, amphotericin B dissolved in DMSO was added to a 5% dextrose solution. An immediate precipitate formed. Therefore, although DMSO solubilizes amphotericin B, such a solution cannot be used in vivo because the DMSO-solubilized amphotericin B will precipitate out in plasma.

7.3. REDUCED TOXICITY OF AMPHOTERICIN B LIGAND PREPARATIONS

The toxicity of the amphotericin B preparations were evaluated in mice.

7.3.1. TOXICITY OF PEG-CHOLESTEROL

Six male Swiss-Webster mice weighing 27 gms each were given a single intravenous injection of 400 mg/kg PEG-cholesterol. No overt signs of toxicity were demonstrated by the mice over a one-month period of visual observation.

7.3.2. COMPARISON OF TOXICITY OF AMPHOTERICIN B AND AMPHOTERICIN B/PEG-CHOLESTEROL

Solutions of Fungizone and solutions of AmB/PEG-cholesterol were prepared such that the concentrations of amphotericin B ranged from 0.625 mg/ml to 1.25 mg/ml. These preparations were inoculated intravenously (in approximately 0.2 ml injections) in male Swiss Webster mice (average weight approximately 35 g). The animals were observed for survival. The percent mortality was plotted against the log dose to determine the LD$_{50}$ for Fungizone and for the AmB/PEG-cholesterol preparations. The LD$_{50}$ of Fungizone was 3.8 mg/kg, whereas the LD$_{50}$ of AmB/PEG-cholesterol was 10.0 mg/kg. Therefore, the AmB/PEG-cholesterol preparation is less toxic than the Fungizone. In fact when compared to Fungizone, the effective dose of the amphotericin B can be increased about 2.5 times when the amphotericin B is administered with the PEG-cholesterol.

7.3.3. TOXICITY OF VARIOUS AMPHOTERICIN B PREPARATIONS IN MICE

To determine the toxicities of various amphotericin B preparations in mice, the following solutions were prepared in distilled water and administered intravenously in mice:

(1) 7 mg/ml of AmB plus 50 mg/ml of PEG-cholesterol (PEG-Chol);

(2) 7 mg/ml AmB plus 7 mg/ml deoxycholate (DOC);

(3) 7 mg/ml AmB plus 7 mg/ml DOC plus 9 mg/ml PEG-Chol; and (4) 7 mg/ml DOC.

Each solution was inoculated into the tail vein of female adult Swiss Webster mice (in groups of four mice, weight 23 g each). The animals were then observed for appearance of blue tail which may indicate a breakdown of the complex, resulting in the precipitation of amphotericin B and subsequent blockage of the blood vessel.

The results of the treatment are shown in Table V.

TABLE V

CONDITIONS OF MICE FOLLOWING ADMINISTRATION OF VARIOUS AMPHOTERICIN B PREPARATIONS

| Group | Inoculum | Appearance of Blue Tail in Each Group of 4 Mice[1] |
|---|---|---|
| 1 | AmB + PEG—Chol | − − − − |
| 2 | AmB + DOC | + + + + |
| 3 | AmB + DOC + PEG—Chol | − − − + |
| 4 | DOC | − − − * |

[1] + designates one mouse with discoloration extending the length of the tail.
− designates one mouse with no tail discoloration.
* designates one mouse with discoloration limited to the tip of the tail.

The appearance of blue tail in the mice is evidence of precipitated material clogging an artery in the tail. Thus, in Group 1, the total absence of blue color in tails indicates that a solution of amphotericin B and PEG-cholesterol forms a stable complex; i.e., one which does not precipitate out of serum. For group 2, blue tails in all the mice indicate that a solution of amphotericin B and deoxycholate precipitates out of sera and blocks the tail artery. A lower incidence of blue tails in Group 3 indicates that PEG-cholesterol lessens the amount of precipitation of an AmB-DOC solution. Finally, deoxycholate by itself (as shown for Group 4) is responsible for a limited blue tail effect.

Thus, the results in Table V tend to show that the mechanism of toxicity could be mediated through binding in situ to low affinity lipid toxicity receptors in the tail and that this toxicity can be attenuated (as shown for Group 1) by preincubation in vitro of the drug with its toxicity receptor.

7.3.4. REDUCED TOXICITY OF AMPHOTERICIN B PREPARATIONS IN CELL CULTURE

Five preparations of amphotericin B were studied to determine the effect each preparation had on cell growth. The preparations were as follows:

1) AmB/PEG-Chol (1:3.9), (AmB:PEG-cholesterol in a 1:3.9 ratio);
2) AmB/PEG-Chol (1:14), (AmB:PEG-cholesterol in a 1:14 ratio);
3) AmB plus DOC (Fungizone);
4) PEG-cholesterol;
5) DOC.

The minimum inhibitory concentration (M.I.C.) of the amphotericin B preparations for *C. albicans* was determined as follows: each of the 5 preparations was serially diluted in a 96 round-bottomed well plate, using ½ step dilutions of drug in 50 μl Mico-broth per well and 3 wells for each dilution step. After dilutions were completed, each well received 50 μl broth containing 10$^3$ cells of *C. albicans*. Plates were incubated overnight at 35° C. in a humidified atmosphere. The endpoint of M.I.C. was determined as the maximum dilution of the drug showing 50% growth inhibition in comparison with control well cultures containing no drug, and, therefore, demonstrating 100% growth.

Cytotoxicity for L-cells was also determined in 96 flat-well plates. The drug was diluted serially ($\frac{1}{2}$ step dilutions) in 50 μl of Eagle's Minimum Essential Medium (MEM) containing 10% fetal bovine serum. Then each well received a 50 μl aliquot from a suspension of $3\times10^5$ L-cells/ml medium. After incubation for 72 hours at 37° C. in a humidified atmosphere of 5% $CO_2$ in air, the L-cell monolayers were fixed with 5% formaldehyde and stained with 0.02% crystal violet in 5% formaldehyde. The endpoint was determined as the maximum dilution of the drug showing 50% growth inhibition in comparison with the control well cultures (no drug, 100% growth). The results of these experiments are shown in Table VI.

TABLE VI

INHIBITION OF CELL GROWTH BY DIFFERENT PREPARATIONS OF AMPHOTERICIN B

| | Preparation | Minimum Inhibitory Concentration of Amphotericin B (μg/ml) | |
|---|---|---|---|
| | | C. albicans | L cells |
| (1) | AmB:PEG—Chol (1:3.9) | 0.2 | 166.6 |
| (2) | AmB:PEG—Chol (1:14) | 0.2 | 166.6 |
| (3) | AmB plus DOC (Fungizone) | 0.4 | 62.5 |
| (4) | PEG-Cholesterol | 25,000+ | 500.0+ |
| (5) | DOC | 5,000+ | 250.0 |

The results in Table VI demonstrate that the MIC for the AmB/PEG-cholesterol preparations is approximately 2.7 times greater than the MIC for Fungizone, i.e., Fungizone inhibits cell growth at lower concentrations than AmB/PEG-cholesterol. Therefore, the AmB/PEG-cholesterol preparations are less cytotoxic than Fungizone.

Plastic petri dishes (35 mm diameter) were seeded with 50 L-cells per dish in 2 ml MEM plus 10% fetal calf serum containing one of the amphotericin B preparations (2 dishes per amphotericin B preparation). The dishes were incubated for 10 days and the cloned cultures were stained with crystal violet as described above. The results are shown in Table VII.

TABLE VII

EFFECT OF DIFFERENT AmB PREPARATIONS ON CLONING EFFICIENCY OF L CELLS

| | Number of Clones | | Size of Colonies | |
|---|---|---|---|---|
| Preparation[1] | Number of Colonies | % of Control | Mean Diameter | % of Control |
| AmB/PEG—Chol (1:3.9) | 75 | 78.5 | 1.8 | 72 |
| AmB/PEG—Chol (1:14) | 66 | 68.8 | 1.8 | 72 |
| AmB plus DOC (Fungizone) | 53 | 55.2 | 1.5 | 60 |
| DOC | 68 | 70.8 | 2.3 | 92 |
| PEG—Chol | 83 | 86.5 | 2.5 | 100 |
| Control | 96 | 100.0 | 2.5 | 100.0 |

[1]All three preparations of AmB were added to a final concentration of 25 μg amphotericin B/ml medium.

The results in Table VII also confirm that the AmB/PEG-cholesterol preparations are less cytotoxic than Fungizone.

7.3.5. COMPARISON OF HEMOLYTIC PROPERTIES OF AMPHOTERICIN B PREPARATIONS

The commerical Fungizone preparation causes a significant lysis of red blood cells whereas the amphotericin B/PEG-cholesterol preparations of the present invention do not. This property makes the amphotericin B/PEG-cholesterol preparations more suitable for use in vivo. Details of the experiments are described below.

Equal aliquots of a final suspension of 2% fresh erythrocytes were mixed with serial dilutions of either Fungizone (i.e., amphotericin B with deoxycholate), amphotericin B/PEG-cholesterol (prepared as previously described), PEG-cholesterol, or deoxycholate in phosphate buffered saline free of $Ca^{++}$ and $Mg^{++}$; the mixtures were incubated at 37° C. for 20 hours after which the cells were pelleted by centrifugation and the released hemoglobin in the supernatants was determined spectrophotometrically at an $OD_{550nm}$. Results are presented in Table VIII.

The results in Table VIII clearly demonstrate that the AmB/PEG-cholesterol preparation is less hemolytic than equal concentrations of amphotericin B as a Fungizone preparation.

TABLE VIII

HEMOLYTIC EFFECT OF DIFFERENT PREPARATIONS OF AMPHOTERICIN B

| Concentration[1] (μg/ml) | $OD_{550\,nm}$ | | | |
|---|---|---|---|---|
| | AmB/DOC | AmB/ PEG—Chol | DOC | PEG—Chol |
| 0 | 0.00 | 0.00 | 0.00 | 0.00 |
| 1 | 0.25 | 0.03 | 0.03 | 0.03 |
| 2 | 0.88 | 0.05 | 0.03 | 0.03 |
| 2.5 | 0.28 | 0.06 | 0.03 | 0.03 |
| 15 | 1.5+ | 0.24 | 0.03 | 0.03 |
| 30 | 1.5+ | 0.44 | 0.03 | 0.03 |
| 60 | 1.5+ | 0.90 | 0.06 | 0.03 |
| 125 | 1.5+ | 1.16 | 0.23 | 0.03 |
| 250 | 1.5+ | 1.38 | 0.47 | 0.03 |

[1]The concentration refers to the concentration of AmB when present in the preparation (i.e., in AmB/DOC, and AmB/PEG—Chol preparations). Concentration of the preparations containing no amphotericin B (i.e., DOC, and PEG—Chol) refers to the concentration of the PEG-Cholesterol or deoxycholate in equivalents.

We claim:

1. A drug preparation of reduced toxicity, comprising: a mixture of (a) a pharmaceutically active therapeutic drug which exhibits toxic effects in humans or animals by binding to a toxicity receptor, the drug being selected from the group consisting of the polyene or polyene macrolide antibiotics, anthracyclines, and cisplatin, and (b) a ligand capable of preventing binding of the drug to the toxicity receptor in vivo while allowing the drug to retain its pharmaceutical activity, the ligand being a phospholipid when the drug is an anthracycline or cisplatin, and the ligand being a sterol or water soluble derivative thereof when the drug is a polyene macrolide antibiotic, wherein the drug to ligand ratio reduces the toxicity of the drug in vivo and wherein the preparation is substantially free of liposomes.

2. The drug preparation according to claim 1 wherein the mixture is a solution.

3. The drug preparation according to claim 1, wherein the pharmaceutically active therapeutic drug is lipophilic.

4. The drug preparation according to claim 1 wherein the water soluble sterol is polyethylene glycol-cholesterol.

5. The drug preparation according to claim 1 wherein the drug is a polyene or polyene macrolide antibiotic and the ligand is a sterol or water soluble derivative thereof capable of blocking binding of said polyene or polyene macrolide antibiotic to its toxicity receptor.

6. The drug preparation according to claim 5 wherein the water-soluble sterol is a water soluble cholesterol.

7. The drug preparation according to claim 6 wherein the water soluble cholesterol is polyethylene glycol-cholesterol.

8. The drug preparation according to claim 6 wherein the water-soluble cholesterol is cholesterol hemisuccinate.

9. The drug preparation of claim 5 wherein the mole ratio of antibiotic to ligand is from about 1:1 to about 1:14.

10. The drug preparation of claim 9 wherein the mole ratio of antibiotic to ligand is about 1:1.

11. The drug preparation of claim 10 wherein the sterol is cholesterol.

12. The drug preparation of claim 9 wherein the mole ratio of antibiotic to ligand is about 1:5.

13. The drug preparation of claim 9 wherein the mole ratio of antibiotic to ligand 1:5.9.

14. The drug preparation of claim 9 wherein the mole ratio of antibiotic to ligand is about 1:1.6.

15. The drug preparation of claims 5 or 9 wherein the antibiotic is amphotericin B.

16. The drug preparation of claim 15 wherein the sterol is cholesterol.

17. The drug preparation according to claim 5, wherein said polyene macrolide antibiotic is amphotericin B or a pharmaceutically active salt thereof.

18. The drug preparation of reduced toxicity of claim 5, wherein said ligand is at a concentration below the concentration needed to form liposomes.

19. The drug preparation of claim 18 wherein the sterol or water soluble derivative thereof is cholesterol.

20. The drug preparation of claim 19 wherein the polyene or polyene macrolide antibiotic is amphotericin B.

21. The drug preparation of claim 20 wherein the mole ratio of amphotericin B to the sterol or water soluble derivative thereof as ligand is from 1:1 to about 1:14.

22. The drug preparation of claim 21 wherein the mole ratio of amphotericin B is about 1:1.

23. The drug preparation of claim 22 wherein the mole ratio of amphotericin B is about 1:5.

24. The drug preparation according to claim 1, wherein the drug is cisplatin, and the ligand is a phosphate ester, phosphate anhydride or sulfatide capable of blocking binding of cisplatin to its toxicity receptor.

25. The drug preparation according to claim 24, wherein said ligand is lysophosphatidylcholine.

26. The drug preparation according to claim 24, wherein said ligand is phosphorylcholine.

27. The drug preparation according to claim 24, wherein said ligand is phosphorylserine.

28. The drug preparation according to claim 24, wherein said ligand is phosphorylglyceric acid.

29. The drug preparation according to claim 24, wherein said ligand is inositol monophosphate.

30. The drug preparation according to claim 24, wherein said ligand is inositol biphosphate.

31. The drug preparation according to claim 24, wherein said ligand is inositol triphosphate.

32. The drug preparation according to claim 24, wherein said ligand is inositol tetraphosphate.

33. The drug preparation according to claim 24, wherein said ligand is inositol pentaphosphate.

34. The drug preparation according to claim 24, wherein said ligand is inositol hexaphosphate.

35. The drug preparation according to claim 24, wherein said ligand is a nucleotide.

36. The drug preparation according to claim 24, wherein said ligand is phosphatidylinositol phosphate.

37. The drug preparation according to claim 24, wherein said ligand is phosphatidylinositol bisphosphate.

38. The drug preparation according to claim 24, wherein said ligand is phosphorylinositol.

39. The drug preparation according to claim 24, wherein the drug is triphosphorylinositol.

40. The drug preparation according to claim 1, wherein the drug is an anthracycline and the ligand is cardiolipin, cardiolipin head group, phosphatidylserine, phosphorylserine, phosphatidic acid or tripolyphosphate, wherein the preparation is substantially free of liposomes.

41. A drug preparation of reduced toxicity comprising a polyene or polyene macrolide antibiotic and a ligand wherein the ligand is a sterol or water soluble derivative thereof.

42. The method for administering a drug preparation of reduced toxicity, comprising: administering to an animal or human a therapeutically effective amount of a solution of claim 2.

43. A method for safely administering a polyene or polyene macrolide antibiotic for the treatment of fungal infections, comprising: administering to an animal or human having a fungal infection a therapeutically effective amount of a drug preparation, comprising a mixture of (a) a polyene or polyene macrolide antibiotic and (b) a cholesterol or sterol or a water soluble derivative thereof.

44. The method according to claim 43, wherein the polyene macrolide antibiotic is amphotericin B.

* * * * *

UNITED STATES PATENT AND TRADEMARK OFFICE
CERTIFICATE OF CORRECTION

PATENT NO. : 5,059,591
DATED : October 21, 1991
INVENTOR(S) : Janoff et al.

It is certified that error appears in the above-identified patent and that said Letters Patent is hereby corrected as shown below:

Claim 1, column 20, line 57,
after "a" insert-- polyene or--

Signed and Sealed this

Eighth Day of June, 1999

Attest:

Q. TODD DICKINSON

Attesting Officer

Acting Commissioner of Patents and Trademarks

REEXAMINATION CERTIFICATE (4057th)
United States Patent [19]
Janoff et al.

[11] B1 5,059,591
[45] Certificate Issued Apr. 25, 2000

[54] DRUG PREPARATIONS OF REDUCED TOXICITY

[75] Inventors: Andrew S. Janoff, Yardley, Pa.; Mircea C. Popescu, Plainsboro, N.J.; Carl R. Alving, Bethesda, Md.; Michael W. Fountain, Farragut, Tenn.; Robert P. Lenk, The Woodlands, Tex.; Marc J. Ostro, Princeton, N.J.; Paul A. Tremblay, Hamilton, N.J.; Alan L. Weiner, Lawrenceville, N.J.

[73] Assignee: Liposome Company, Inc., Princeton, N.J.

Reexamination Request:
No. 90/005,227, Jan. 22, 1999

Reexamination Certificate for:
Patent No.: 5,059,591
Issued: Oct. 22, 1991
Appl. No.: 07/405,623
Filed: Sep. 12, 1989

Related U.S. Application Data

[63] Continuation of application No. 06/844,248, Mar. 24, 1986, Pat. No. 4,897,384, which is a continuation of application No. 06/604,503, May 2, 1984, abandoned, which is a continuation-in-part of application No. 06/498,268, May 26, 1983, abandoned.

[51] Int. Cl.[7] ................ A61K 31/70; A61K 31/685; A61K 31/015; A61K 35/00
[52] U.S. Cl. ................ 514/31; 514/78; 514/766; 424/116; 424/450
[58] Field of Search ................ 514/25, 27, 29, 514/31, 34, 76, 78, 786, 766; 424/116, 450

[56] References Cited

PUBLICATIONS

Bittman et al., "Fluorescence Studies of the Binding of Polyene Antibiotics Filipin III, Amphotericin B, Nystatin and Lagosin to Cholesterol", *Proc. Nat. Acad. Sci. USA* 69(12):3795–3799 (1972) ("Bittman").

Brockerhoff et al., "Preparation and Structural Studies of Cholesterol Bilayers", *Biochim. Biophys. Acta* 691:227–232(1982) ("Brokerhoff").

Chen et al., "Kinetics of Association of Amphotericin B with Vesicles", *Biochem.* 16(19):145–149 (1977) ("Chen").

DeKruijff et al., "Polyene Antibiotic–Sterol Interactions In Membranes of *Acholeplasma laidlawii* Cells And Lecithin Liposomes. III Molecular Structure of the Polyene Antibiotic–Cholesterol Complexes", *Biochim. Biophys. Acta* 339:57–70 (1974) ("De Kruijff").

Ernst et al., "Interaction d'un heptaene antifongique, l'amphotericine B, avec le cholesterol in vitro, dJtectJe par dichr`isme circulaire et absorption Influnce de la temperature", *Comptes Rendus Des SJances De AcadJmie Des Sciences*—Serie D 289:1145–1148 (1979) ("Ernst").

Gent et al., "Interaction of the Polyene Antibiotics With Lipid Bilayer Vesicles Containing Cholesterol", *Biochim. Biophys. Acta* 426:17–30 (1976) ("Gent").

Graybill et al., "Treatment of Murine Cryptococcosis With Liposome–Associated Amphotericin B", *J. Infec. Dis.* 145:748–752 (1982) ("Graybill").

Gruda et al., "Application of Differential Spectra In the Ultraviolet–Visible Region to Study the Formation of Amphotericin B–Sterol Complexes", *Biochim. Biophys. Acta* 602:260–268 (1980).

Kotler–Brajtburg et al., "Molecular Basis For The Selective Toxicity of Amphotericin B For Yeast and Filipin For Animal Cells", *Antimicrol. Aq. Chemother.* 5(4):377–382 (1974) ("Kotler–Brajtburg").

Norman et al., Studies on the Biological Properties of Polyene Antibiotics: Comparison of Other Polyenes With Filipin In Their Ability To Interact Specifically with Sterol, *Biochim. Biophys. Acta* 290:1–14 (1972) ("Norman").

Patterson et al., "Studies On the Competition of Polyene Antibiotics For Sterols", *J. Antibiot.* 32:646–653 (1979) ("Patterson").

Schroeder et al., "Fluorometric Investigations of the Interaction of Polyene Antibiotics With Sterols", *Biochem.* 11(16):3105–3111 (1972) ("Schroeder").

Medoff et al., "Antifungal Agents Useful In Therapy of Systemic Fungal Infections", *Ann. Rev. Pharmacol. Toxicol.* 23:303–330 (1983) ("Medoff").

New et al., "Antileischmanial Activity of Amphotericin and Other Antifungal Agents Entrapped in Liposomes", *J. Antimicrobiol. Chemother.* 8:371–381 (1981) ("New").

Taylor et al., Amphotericin B in Liposomes : A Novel Therapy for Histoplasmosis, *Am. Rev. Respir.* 125: 610–611 (1982) ("Taylor").

Primary Examiner—Kathleen Kahler Fonda

[57] ABSTRACT

Preparations of drugs in admixture with certain ligands are described which, when administered to animals or humans, are less toxic than conventional drug preparations. Although the toxicity of the drug-ligand preparations described is greatly reduced, the drug retains pharmacological activity.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5, 13, 19, 21–23, 41 and 43 are determined to be patentable as amended.

Claims 2–4, 6–12, 14–18, 20, 24–40, 42 and 44, dependent on an amended claim, are determined to be patentable.

New claims 45 and 46 are added and determined to be patentable.

1. A drug preparation of reduced toxicity, comprising: a mixture of (a) a pharmaceutically active therapeutic drug which exhibits toxic effects in humans or animals by binding to a toxicity receptor, the drug being selected from the group consisting of the polyene or polyene macrolide antibiotics, anthracyclines, and cisplatin, and (b) a ligand capable of preventing binding of the drug to the toxicity receptor in vivo while allowing the drug to retain its pharmaceutical activity, the ligand being a phospholipid when the drug is an anthracycline or cisplatin, and the ligand being a [sterol or] water soluble derivative [thereof] *of a sterol* when the drug is a polyene macrolide antibiotic, wherein the drug to ligand ratio reduces the toxicity of the drug in vivo and wherein the preparation is substantially free of liposomes.

5. The drug preparation according to claim 1 wherein the drug is a polyene or polyene macrolide antibiotic and the ligand is a [sterol or] water soluble derivative [thereof] capable of blocking binding of said polyene or polyene macrolide antibiotic to its toxicity receptor.

13. The drug preparation of claim 9 wherein the mole ratio of antibiotic to ligand *is* 1:5.9.

19. The drug preparation of claim 18 wherein the [sterol or] water soluble derivative [thereof] is *a water soluble derivative of* cholesterol.

21. The drug preparation of claim 20 wherein the mole ratio of amphotericin B to the [sterol or] water soluble derivative [thereof] as ligand is from 1:1 to about 1:14.

22. The drug preparation of claim 21 wherein the mole ratio [of amphotericin B] is about 1:1.

23. The drug preparation of claim [22] *21* wherein the mole ratio [of amphotericin B] is about 1:5.

41. A drug preparation of reduced toxicity comprising a polyene or polyene macrolide antibiotic and a ligand wherein the ligand is a [sterol or] water soluble derivative [thereof] *of a sterol, and wherein the preparation is substantially free of liposomes*.

43. A method for safely administering a polyene or polyene macrolide antibiotic for the treatment of fungal infections, comprising: administering to an animal or human having a fungal infection a therapeutically effective amount of a drug preparation, comprising a mixture of (a) a polyene or polyene macrolide antibiotic and (b) a [cholesterol or sterol or] a water soluble derivative [thereof] *of a sterol, wherein the preparation is substantially free of liposomes*.

*45. The drug preparation of claim 41 wherein the water soluble derivative of a sterol is a water soluble derivative of cholesterol, and wherein the polyene or polyene macrolide antibiotic is amphotericin B.*

*46. The method of claim 43 wherein the water soluble derivative of a sterol is a water soluble derivative of cholesterol, and wherein the polyene or polyene macrolide antibiotic is amphotericin B.*

\* \* \* \* \*